(12) United States Patent
Wiese et al.

(10) Patent No.: US 6,500,979 B1
(45) Date of Patent: *Dec. 31, 2002

(54) PROCESS FOR CARRYING OUT CATALYTIC MULTIPHASE REACTIONS, IN PARTICULAR VINYLATIONS OF CARBOXYLIC ACIDS

(75) Inventors: Klaus-Diether Wiese, Haltern (DE); Paul Olbrich, Haltern (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/583,776

(22) Filed: May 31, 2000

(30) Foreign Application Priority Data

Jun. 2, 1999 (DE) .......................................... 199 25 385

(51) Int. Cl.[7] .......................... C07C 69/00; C07C 69/74
(52) U.S. Cl. ........................ 560/129; 560/128; 560/127
(58) Field of Search ................................ 560/129, 128, 560/127

(56) References Cited

U.S. PATENT DOCUMENTS 5,430,179 A  7/1995  Lincoln et al.
5,990,036 A * 11/1999 Deviny

FOREIGN PATENT DOCUMENTS

| DE | 1 210 810 | | 9/1966 |
|---|---|---|---|
| DE | 1 238 010 | | 4/1968 |
| DE | 1 237 557 | | 10/1972 |
| EP | 0 622 352 | | 11/1994 |
| EP | 1 057 524 A2 | | 4/2000 |
| GB | 1125055 | * | 4/1967 |
| WO | 98/16494 | | 4/1998 |

OTHER PUBLICATIONS

US Patent Application 09/585425.*
Ullman's Encyclopedia of Industrial Chemistry, vol. A27, pps. 430–434, "Vinyl Esters," 5th Edition.
S. Ergun, Chemical Engineer Progress, vol. 48, No. 2, pps. 89–94, "Fluid Flow Through Packed Columns," Feb. 1952.
Y. Sato, et al., Journal of Chemical Engineering of Japan, vol. 6, No. 2, pps. 147–152, "Pressure Loss and Liquid Holdup in Packed Bed Reactor with Cocurrent Gas–Liquid Down Flow," 1973.
D.E. Sweeney, AIChE Journal, vol. 13, No. 4, pps. 663–669, "A Correlation for Pressure Drop in Two–Phase Cocurrent Flow in Packed Beds," Jul. 1967.
V.W. Weekman, Jr., et al., A.I.Ch.E. Journal, vol. 10, No. 6, pps. 951–957, Fluid–Flow Characteristics of Concurrent Gas–Liquid Flow in Packed Beds, Nov. 1964.
R.P. Larkins, et al., A.I.Ch.E. Journal, vol. 7, No. 2, pps. 231–239, "Two–Phase Concurrent Flow in Packed Beds," Jun. 1961.
N. Midoux, et al., Journal of Chemical Engineering of Japan, vol. 9, No. 5, pps. 350–356, "Flow Pattern, Pressure Loss and Liquid Holdup Data in Gas–Liquid Downflow Packed Beds with Foaming and Nonfoaming Hydrocarbons," 1976.
G. Huebner, vol. 68, No. 4, pps. 290–292, "Vinylierung Hoeherer Carbonsaeuren An Katalystorschmelzen," 1966.
VDI–Waermeatlas, pps. La1–La2; Lb1–Lb7 and Le1–Le4, "Druckverlust," 1997.

* cited by examiner

Primary Examiner—Alan L. Rotman
Assistant Examiner—Héctor M. Reyes
(74) Attorney, Agent, or Firm—Oblon, Spivak, McClelland, Maier & Neustadt, P.C.

(57) ABSTRACT

Catalytic multiphase reactions are conducted by a process, comprising:
conducting the catalytic multiphase reactions in a tube reactor, wherein the catalyst is present in the continuous phase and at least one starting material is present in a dispersed phase and the loading factor B of the tube reactor is equal to or greater than 0.8.

15 Claims, 4 Drawing Sheets

PROCESS FOR CARRYING OUT CATALYTIC MULTIPHASE REACTIONS, IN PARTICULAR VINYLATIONS OF CARBOXYLIC ACIDS

BACKGROUND OF THE INVENTION

1. Field of the Invention

The present invention relates to a process for conducting catalytic multiphase reactions in a tube reactor. More particularly, the invention relates to a method of preparing vinyl esters by reaction of carboxylic acids with acetylene. Furthermore, the invention relates to the use of the vinyl esters.

2. Description of the Background

Vinyl esters are building blocks for the preparation of copolymers. Vinyl esters of particular industrial importance include those of tertiary $C_{10}$ acids and also those of tertiary $C_9$ acids. These vinyl esters can be copolymerized with vinyl acetate and then serve as a component for paints. Other vinyl esters of importance include those of 2-ethylhexanoic acid, of isononanoic acid, but also of lauric and stearic acids, for example for the production of adhesives.

The reaction of carboxylic acids with acetylene to form vinyl esters has been known for a long time (e.g. G. Hübner, Fette, Seifen, Anstrichm, 68, 290 (1966)), and a review of currently used processes may be found, for example, in Ullman's Encyclopedia of Industrial Chemistry, Fifth Completely Revised Edition, Volume A2, 430–434.

The reaction of acetylene and vinyl esters can be described by the reaction equation:

$R\text{—}COOH + C_2H_2 \rightarrow R\text{—}COO\text{—}CH=CH_2$.

As catalyst, use is usually made of the zinc salt of the carboxylic acid to be reacted, dissolved in excess carboxylic acid (DE 1238010, DE 1210810). In another method, the reaction is carried out in a paraffinic solvent which has a boiling point higher than the reaction temperature to be employed (e.g paraffin oils) and the concentration of carboxylic acid is to be kept below 5% by weight and the zinc content is to be kept in the range from 0.5–5% by weight, based on the reaction solution. The temperatures employed are generally above 200° C., typically from 220–295° C. A considerable molar excess of acetylene over the carboxylic acid to be vinylated has to be employed; values of 5–20 mol. of acetylene per mol. of carboxylic acid to be reacted are typical. This means a high circulation of acetylene with the vinyl ester and unreacted carboxylic acid being discharged with the waste gas as a function of their partial vapor pressure, subsequently condensed and separated from one another by distillation.

The formation of low-boiling by-products such as acetaldehyde can lead to resinification of the catalyst. Furthermore, the formation of high boilers due to polymerization of the vinyl ester formed and also the formation of carboxylic anhydrides which no longer participate in the reaction can lead to a reduction in conversion. This can be corrected only by discharging part of the reaction solution or the zinc salt melt, which in turn requires introduction of fresh catalyst. In the examples in DE 1 237 557, it can be seen that at an appropriately high molar excess of acetylene over carboxylic acids of from 5:1 to 20:1, selectivities of from 74.3 to at most 96.1% are achieved. This corresponds to formation of from 3.9–25.7% of by-products.

In engineering terms, the preparation of vinyl esters is a two-phase reaction in which the acetylene forms the gas phase, and the catalyst phase, the carboxylic acid to be reacted, the vinyl ester and any inert solvent form the liquid phase. In order to achieve high conversions, it is, therefore, necessary to employ measures to bring the phases into intimate contact with one another. Such gas-liquid reactions are customarily carried out in bubble columns or stirred reactors. Trickle reactors are also mentioned in the literature. High pressures are specifically not wanted in reactions with acetylene, since acetylene tends to undergo autodecomposition and a gauge pressure of 300 mbar (absolute pressure= 1.3 bar) must not be exceeded in the case of pure acetylene. This considerably narrows the choice of reactor. Thus, only short bubble columns or stirred reactors having a small height can be used for the vinylation, since even the static pressure of the liquid can require an acetylene admission pressure of greater than 300 mbar. In addition, the high acetylene circulations which may be necessary require continual recompression of the acetylene.

An alternative is the use of more highly compressed acetylene, in which case the decomposition limit has to be lowered by addition of large proportions of inert gases such as nitrogen. This measure leads to problems in the removal of the tailgas and is also not unproblematical in terms of safety.

For this reason, other processes which avoid or reduce these drawbacks have been developed. Thus, EP 0 622 352 uses platinum metal complexes (in particular those of ruthenium) as catalysts for the preparation of vinyl esters, by means of which the reaction temperature was able to be reduced significantly. However, this process is also preferably carried out at a molar ratio of acetylene/carboxylic acid of from 1.5:1 to 10:1 and at acetylene pressures of from 15–20 bar in order to achieve satisfactory space-time yields. The high price of noble metal compounds necessitates complete circulation of the catalyst without it being decomposed or lost by unintended discharges. A further example of the ruthenium-catalyzed preparation of vinyl esters is given in U.S. Pat. No. 5,430,179.

A completely different process for preparing vinyl esters is transvinylation. Here, an industrially readily available vinyl ester such as vinyl acetate is reacted with the acid to be vinylated in the presence of noble metal catalysts such as $Li_2PdCl_4$, forming an equilibrium mixture of vinyl acetate, acetic acid, the carboxylic acid to be reacted and its vinyl ester. Problems here are the difficulty and expense of separating the equilibrium mixtures, the price of vinyl acetate and the formation of contaminated acetic acid.

Taking into account all advantages and disadvantages, the vinylation of carboxylic acids using acetylene in the presence of zinc salts as catalysts, i.e. a multiphase reaction, is on balance the most economical and industrially simplest process.

In the following, the term multiphase reactions is used to describe reactions which proceed with participation of two or more immiscible or only partially miscible fluid phases. This encompasses, for example, reactions between a gas phase and a liquid phase (gl) as in the reaction of acetylene with a carboxylic acid, but also reactions between two liquid phases which are immiscible or have a miscibility gap under the prevailing reaction conditions (ll) and reactions in which both two liquid immiscible or only partially miscible phases and a gas phase participate (gll).

Examples of industrially important gas-liquid reactions (gl) are, apart from the reaction of acetylene with carboxylic acids under consideration here, hydrogenations using homogeneously dissolved catalysts, oxidations using air or oxygen and the hydroformylation of olefins.

Multiphase reactions are generally associated with a series of problems which makes their engineering design significantly more difficult than is the case for simple homogeneous reactions. A few typical problems are described below:

In all cases, the materials have to be brought into very intimate contact with one another in order to minimize the problem of mass transfer: it is necessary to generate a mass transfer area a, between the phases which is as large as possible. On the other hand, the phases have to be able to be separated easily again after the reaction is complete: excessive mixing can lead to problems here. In the presence of two liquid phases, emulsion formation can occur, while in the case of gas-liquid processes it is possible for foaming to occur. In the case of the 3-phase processes mentioned, it is even possible for all of the problems to occur simultaneously.

Apart from a high mass transfer area $a_s$, a very high mass transfer coefficient kit should be achieved in all multiphase reactions. Overall, the KLA value, i.e. the product of $k_l$ and $a_s$ in the mass transfer equation $$j=k_l*a_s*(C*-C)$$

where:

j [mol/s]: the molar flow of reacting component through the phase interface (e.g. entry of acetylene into the catalyst phase), $k_l$ [m/s]: mass transfer coefficient, $a_s$ [m²]: phase interface area in the reactor, C* [mol/m³]: maximum solubility of the starting material in the second phase (e.g. acetylene in the catalyst phase) and C [mol/m³]: actual concentration of the starting material which in turn is coupled to the reaction rate, should be a maximum.

In view of the above, there is a need for a process for carrying out multiphase reactions which avoids the above-mentioned disadvantages and can also be implemented in a simple manner.

SUMMARY OF THE INVENTION

Accordingly, one object of the present invention is to provide a process for conducting multiphase reactions which is suitable, in particular, for the preparation of vinyl esters by catalyzed reaction of carboxylic acids with acetylene.

Briefly, this object and other objects of the present invention as hereinafter will become more readily apparent can be attained by a process for conducting catalytic multiphase reactions, comprising:

conducting the catalytic multiphase reactions in a tube reactor, wherein the catalyst is present in the continuous phase and at least one starting material is present in a dispersed phase and the loading factor B of the tube reactor is equal to or greater than 0.8.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

In technical terms, the novel process should meet the following demands made of multiphase processes:

generation of high and stable mass transfer between the participating phases simplicity of implementation, if possible using customary industrial apparatuses simple and reliable heat removal high operating safety simple and reliable scale-up In respect of the reaction of acetylene with carboxylic acid to be carried out, the following specific requirements are added:

high selectivity, avoidance of, in particular, high-boiling by-products no or only little discharge of catalyst high space-time yield, small reactors high acetylene conversion on a single pass, avoidance of circulation of acetylene simple and safe handling of acetylene high product purity In the process of the invention, we have found a surprisingly simple process for carrying out multiphase reactions which can be carried out in a tube reactor, if desired containing packing or internal fittings, and is suitable for the vinylation of carboxylic acids by acetylene with high space-time yields and selectivities.

The present invention accordingly provides a process for carrying out catalytic multiphase reactions in a tube reactor, wherein the catalyst is present in the continuous phase and at least one starting material is present in a dispersed phase and the loading factor B of the reactor is equal to or greater than 0.8.

In a specific embodiment of the present invention, carboxylic acids are reacted with acetylene by means of the multiphase reaction to give the corresponding vinyl esters.

The process of the invention is suitable for the vinylation of carboxylic acids; these may contain from 2–16, preferably from 4–13, carbon atoms. Particular preference is given to using pivalic acid ($C_5$), 2-ethylhexanoic acid ($C_8$), neo-nonanoic acid ($C_9$), decanoic acid ($C_{10}$), undecanoic acid ($C_{11}$), lauric acid ($C_{12}$) or tridecanoic acid ($C_{13}$).

As already mentioned, the tube reactor can contain packing or internal fillings. For the purposes of the present invention, packing encompasses, for example: Raschig rings, saddles, Pall rings, tellerettes, wire mesh rings or woven wire mesh. Examples of internal fillings are filter plates, baffles, column trays, perforated plates or other mixing devices. However, for the purposes of the present invention, internal fillings can also comprise a plurality of narrow, parallel tubes to form a multitude reactor. Particular preference is given to structured mixer packings or demister packings.

In the process of the invention, it is also of critical importance to adhere to or exceed a minimum cross-sectional throughput of the tube reactor. In upflow operation of the reactor (flow direction from the bottom to the top), the flooding point should be exceeded. The reactor is thus operated above the point at which bubble columns are usually operated. In downflow operation (flow direction from the top to the bottom), the cross-sectional throughput must be set so that the reactor is completely flooded. Thus, the process is operated above the point at which it would be possible to speak of a trickle bed.

To fix the minimum necessary loading of the reactor more precisely, the loading factor B of the tube reactor is calculated as a dimensionless pressure drop $$B = PD/PS$$

where PD [Pa/m] is a pressure drop per unit length over the reactor under operating conditions and PS [Pa/m] is a mathematical parameter having the dimensions of a pressure per unit length, defined as the ratio of mass flow M [kg/s] of all components in the reactor to the volume flow V [m$^3$/s] of all components under operating conditions, multiplied by g=9.81 m/s$^2$, i.e. PS=(M/V)*g.

PS would be the static pressure per meter of a multiphase mixture in an upright tube if all phases were to flow at the same velocity. PS is a purely mathematical parameter which is derived from the mass flows fed to the reactor and is independent of the flow direction in the reactor, the flow velocity of all phases or the flooding state of the reactor.

The pressure drop PD [Pa/m] is used as a mathematical parameter to fix the process conditions and can be calculated by established methods for single-phase or multiphase flows. Appropriate methods of calculating the pressure drop PD in tubes, internal fittings or packed beds, etc. may be found, for example, in the VDI-Warmeatlas, 7th augmented edition, VDI-Verlag GmbH, Düsseldorf 1994, Sections La1 to Lgb7, and also in the standard work by Heinz Brauer, Grundlagen der Einphasen- und Mehrphasenstromungen, Verlag Sauerländer, Aarau and Frankfurt am Main, 1971.

The pressure drop PD in the case of single-phase flow through an empty tube is given by:

$$PD = Cw * \rho/2 * Cw^2 / D$$

where:
- $\rho$ [kg/m$^3$]: density of the flowing medium under operating conditions,
- w [m/s]: flow velocity (volume flow/cross-sectional area),
- D [m]: tube diameter end
- Cw [-]: resistance coefficient of the tube through which flow occurs.

In the case of flow through packing, beds or internal fittings, the velocity w is to be replaced by the effective velocity (w/ψ) and the tube diameter D is to be replaced by the hydraulic channel diameter $d_H$ of the packing or internal fittings, so that:

$$PD = Cw * \rho/2 * (W/\psi)^2 * 1/d_H$$

where:
- $d_H$ [m]: hydraulic channel diameter
- ψ [-]: empty tube fraction
- Cw [-]: resistance coefficient of the apparatus with filling through which flow occurs.

The packing-related data $d_H$ and ψ are frequently part of the delivery specifications for packing. For a series of packings, data are given in the abovementioned VDI-Warmeatlas.

The empty tube fraction ψ can also be determined experimentally by, for example, measuring the volume of the reactor before and after filling with the packing. The hydraulic channel diameter can in turn be calculated, if it is not known, from the specific surface area F [m$^2$/m$^3$] of the packing or internal fittings (generally known or able to be determined experimentally) using the simple relationship $$d_H = 4\psi/F.$$

The resistance coefficient of tubes, internal fittings and packing is generally described as a function of the Reynolds number Re which gives information about the flow state under the chosen conditions. In the case of packing, internal fittings, etc., the following relationship can almost always be employed:

$$Cw = K_1/Re^n + K_2/Re^m$$

where frequently employed exponents are n=1, m=0 (method of S. Ergun, Chem. Engog. Progr. 48, (1948), 89), or n=1, m=0.1 (method of Brauer et al.). $K_1$ and $K_2$ are packing-related constants which are known from supply data or from the literature (examples may be found in the VDI-Warmeatlas and in Brauer et al.). However, they can also be determined experimentally by passing a liquid through the tube reactor containing packing at various velocities and determining Cw as a function of Re from the known data and the measured pressure drop.

Finally, the dimensionless Reynolds number Re is defined as $$Re = w * (\rho/\eta) * D \text{ for empty tubes}$$

or $$Re = (w/\psi) * (\rho/\eta) * d_H \text{ for tubes}$$

containing internal fittings or packing. In each case, η[Pa*s] is the viscosity and ρ[kg/m$^3$] is the density of the flowing medium.

In the case of two-phase flows (here gas-liquid for acetylene/carboxylic acid), the pressure drop increases over proportionally. Usually, using the Lockhart-Martinelli method (in Brauer et al.), the pressure drop of the two-phase flow $P_{lg}$ is expressed in relation to the pressure drop of one of the two phases, for example to the pressure drop of the pure flowing liquid phase $P_l$, and expressed in relation to the pressure drop of the two phases $P_l$ and $P_g$ regarded as flowing alone.

To calculate pressure drops in two-phase flows, use is frequently made of the dimensionless pressures $\phi^2 = P_{lg}/P_l$ and $X^2 = P_l/P_g$. The further relationship $\phi^2 = \text{function}(X^2)$ has frequently been examined. Examples may be found in the following literature references:

Y. Sato, T. Hirose, F. Takahashi, M. Toda: "Pressure Loss and Liquid Hold Up in Packed Bed Reactor with Cocurrent Gas-Liquid Down Flow"; J. Chem. Chem. Eng. Of Japan, Vol. 6 (No. 2), 1973, 147–152;

D. Sweeney: "A Correlation for Pressure Drop in Two-Phase Concurrent Flow in Packed Beds"; AlChE-Journal, Vol. 13, 7/1967, 663–669;

V. W. Weekman, J. E. Myers: "Fluid-Flow Characteristics of Concurrent Gas-Liquid Flow in Packed Beds"; AlChE-Journal, Vol. 10 (No. 6), 11/1964, 951–957;

R. P. Larkins, R. P. White, D. W. Jeffrey: "Two-Phase Concurrent Flow in Packed Beds"; AlChE-Journal, Vol. 7 (No. 2), 6/1961, 231–239 or N. Midoux, M. Favier, J.-C. Charpentier: "Flow Pattern, Pressure Loss and Liquid Holdup Data in Gas-Liquid Down-Flow Packed Beds with Foaming and Nonfoaming Liquids"; J. Chem. Eng. Of Japan, Vol. 9 (No. 5), 1976, 350–356.

The relationship proposed by Midoux, which has been tested for many gas-liquid systems, is frequently utilized for the calculation. In the case of nonfoaming systems, for example:

$$\phi^2 = 1 + 1/X + 1.14/X^{0.54}.$$

This so-called Lockart-Martinelli relationship is depicted in graphical form in many works; detailed descriptions of it may be found in many text books on process engineering and publications, for example in Brauer et al.

The pressure drop of the multiphase flow $P_{lg}$ is then derived from the experimentally determined pressure drop, or the pressure drop estimated as described above, of the pure flowing liquid phase $P_l$ using $$P_{lg} = \phi^{2*} P_l,$$

and expressed as a function of the reactor length L [m]

$$PD = P_{lg}/L.$$

The pressure drop of a multiphase flow can thus be calculated by customary methods of chemical engineering. The same applies to the previously defined dimensionless pressure drop B. i.e. the loading factor of the multiphase reactor.

The magnitude of the dimensionless loading factor B is a necessary fundamental condition in the process of the invention; B should be greater than or equal to 0.8, preferably greater than or equal to 0.9 or particularly preferably greater than or equal to 1. In the region where B is greater than or equal to 0.8, a reactor operated from the top downward begins to flood. It may be expressly pointed out that when these conditions are adhered to, the advantages of the process of the invention are achieved even when the reactor is operated from the bottom upward or in another direction.

Higher cross-sectional loadings of the reactor (B>>1), recognizable by the increasing differential pressure over the reactor, are possible at any time and even desirable as long as the increasing space-time yields justify the similarly increasing energy consumption. An upper limit is, therefore, imposed only by practical considerations such as energy consumption or difficulty of separating the phases after the reactor is complete.

It can thus be seen that, apart from the volume flows of the individual phases or the empty tube velocities $w=V/(\pi D^2/4)$ derived therefrom, the physical dimensions of the reactor (length L, diameter D) and, in particular, the data for the packing used (hydraulic diameter $d_H$, empty tube fraction $\psi$) play an important role. Correct selection of these parameters enables the process to be matched without difficulty to a wide variety of requirements; it is only important to adhere to the condition $B \geq 0.8$, preferably $B \geq 0.9$ and particularly preferably $B \geq 1$.

In the case of a slow reaction, one will, for example, select a small hydraulic diameter of the packing or select a large specific surface area, so that the required conditions for B are achieved even at small flow velocities. In this way, sufficient residence times over the length of a sensibly dimensioned industrial reactor are obtained. In the case of very fast reactions, a converse procedure is advisable.

A further criterion in carrying out the process of the invention is the ratio of the mass flow of the liquid, catalyst-containing phase $M_1$ to the mass flow of the disperse phase or phases $M_2$. In the case of the vinylation of carboxylic acids, the mass flow of the catalyst phase $M_1$ is significantly greater than the mass flow of the disperse phase, i.e. the acetylene phase $M_2$. In the process of the invention, the mass ratio $M_1/M_2$ of the continuous phase ($M_1$) to the disperse phases ($M_2$) can be greater than 2; it is preferred that $M_1/M_2 > 10$. Flow ratios of $M_1/M_2 > 100$ are quite possible and frequently even advantageous. Under the condition $M_1/M_2 > 2$, the catalyst phase is the continuous phase, while the disperse phase is divided into fine bundles or into fine droplets. In the process of the invention, it is possible for at least one starting material to be dispersed by means of the energy introduced into the tube rector by the continuous phase. This leads to dispersion of at least one starting material in bubbles or droplets within the continuous catalyst phase.

This, too, can be estimated using customary engineering methods. Suitable methods employ relationships involving dimensionless parameters, for example $$d_s/d_H = k * Re_{gl}^m * We_{gl}^n$$

where:

$d_s$: diameter of the droplets or bubbles obtained by the Sauter method (in Brauer et al.), $d_H$: hydraulic diameter of the packing, $Re_{gl}$: Reynolds number of the multiphase flow $= w_{gl} * (\rho_l/\eta_l) * (d_H/\psi)$, $We_{gl}$: Weber number of the multiphase flow $= w_{gl} * (\rho_l/\sigma_{gl}) * (d_H/\psi^2)$, k,m,n: empirical constants (known or determined by experiments), w: empty tube velocity [m/s]$=V/(\pi D^2/4)$, V: volume flow under operating conditions [m³/s], $\rho$: density under operating conditions [kg/m³], $\eta$: viscosity under operating conditions [Pa*s] and $\gamma$: interfacial tension under operating conditions [N/m] and the indices I (liquid phase), g (gas phase) and gl (gas/liquid two-phase flow).

In the case of structured packings such as Sulzer SMV or narrow tubes as internal fittings, it seems plausible that a calculated bubble or droplet diameter d, greater than the channel diameter is not sensible. However, this does not apply to permeable packings and packing elements such as wire mesh rings or woven wire mesh (known as demister packings or droplet precipitators). In the process of the invention, it is possible to use calculated droplet diameters which are at least equal to or smaller than the hydraulic channel diameter:

$$d_s/d_H \leq 1, \text{ preferably } <0.9.$$

The calculated droplet diameter finally allows a mass transfer area to be calculated in accordance with:

$$As = 6\phi_g d_s [m^2/m^3].$$

For the phase fraction $\phi_g$ of the disperse phase (in the case of the vinylation, the gas phase or the acetylene is dispersed), the ratio of the empty tube velocities of the phases can be used:

$$\phi_g \sim w_g/w_{gl}.$$

The residence time τ of the phases flowing through the reactor can be calculated approximately as $\tau \sim L*\psi_{lg}$. The residence time τ in the process of the invention is generally much less than one hour and can be in the minute range or even lower. Nevertheless, this completely unusual method of operation (high catalyst throughput in the reactor, comparatively low proportion of starting material in the reaction composition, and as a result a very short residence time) surprisingly achieves high space-time yields in the case of many multiphase reactions. Alternatively, at the same space-time yields it is possible to work at significantly lower temperatures than is customary, since the increase in the reaction rate, which can, for example, result in minimization of secondary reactions and thus improve selectivity, makes this economically feasible.

The process of the invention can be matched very flexibly to a wide variety of requirements. For specific requirements, the following embodiments of the process of the invention are possible:

If the application requires a very long mixing zone or calming zones are required, for example for decreasing mass flows, a cascaded arrangement of tube reactors having internal fittings or packing can be employed.

A cascaded arrangement of tube reactors or the alternative arrangement of packed and empty tube sections is advisable if a particularly low pressure drop is desired.

Furthermore, parallel arrangement of tube reactors or the use of a multitude reactor, in which the tubes can assume the function of internal fittings, is conceivable. In addition, reactors can be provided with multiple feed points for gas along the length of the reactor if the gas consumption is so high that unfavorable phase ratios of gas to liquid result from the two phases being combined upstream of the reactor.

The particular conditions of the process of the present invention allow further embodiments of the process. Thus, the high circulation of the catalyst phase or of the continuous phase which is necessary can additionally be exploited for operating a jet nozzle which is arranged as a liquid-jet gas compressor upstream of the actual tube reactor. This can be used for thorough premixing of the two phases and for compressing the gas phase, which makes the operation mode with higher prepressures in the reactor possible. Finally, if, conversely, the suction action is exploited instead of compressing the gas, it is even possible to circulate gas with simultaneous premixing of the phases. The energy introduced into the tube reactor by means of the catalyst-containing continuous phase can be used for dispersing the starting material phase or at least one starting material.

In the case or reactions with acetylene, as in the vinylation of carboxylic acids, there is a risk of acetylene decomposition at elevated pressure (without dilution) above 1.3 bar absolute. However, this does not apply to acetylene which is finely dispersed in a liquid, since possible decomposition in a single bubble is immediately stopped by the surrounding liquid. Since compression occurs in the liquid-jet gas compressor by fine mixing into the driving jet, this makes greater compression of acetylene possible without presenting a danger. If the circulation pump fails, there is insufficient energy for compression, the reactor runs empty and the acetylene liberated is again under atmospheric pressure. Finally, the reactor provided with packing or internal fittings acts like a decomposition barrier, so that double safety is ensured.

Heat removal in the case of strongly exothermic reactions, for example as in the vinylation, is also not critical in the process of the invention. The high throughput of the catalyst circuit acts as a heat exchange medium so that, even in the case of adiabatic operation of the reactor, only small temperature differences arise and a homogeneous temperature distribution in the reactor without temperature peaks results. The heat generated can then conveniently be removed or exploited for energy recovery by means of any conventional heat exchanger located in the external catalyst circuit. To improve removal of heat, it can sometimes be useful to run the catalyst circuit at a higher circulation rate (i.e. at a higher B value) than is necessary according to the experimental results, since the catalyst circuit enables a smaller temperature gradient over the reactor to be set.

Compared to the prior art, the process of the invention offers considerable advantages, for example:

High space-time yields can be achieved at comparatively low temperatures.

The formation of by-products is extremely low; values of 1–2% by weight and less are possible.

The process is gentle on the catalyst and it suffers from very little deactivation; continuous discharge is not necessary.

In the case of the vinylation of carboxylic acids using the process of the invention, there are further advantages:

The conversion of acetylene is very high and can be 98% and more, so that recirculation of acetylene is not necessary. In practice, one will even deliberately set a small waste-gas fraction which is not necessary per se from the point of view of the process, since acetylene contains inert materials which accumulate because of the high conversion and have to be discharged.

The particular mode of operation makes it possible to operate an industrial reactor having a length of many meters despite the low permissible acetylene prepressure of only 300 mbar.

The specific residence time and the loading factor are selected in accordance with the process of the invention. For this purpose, the reaction can be carried out in one or more tube reactors with internal fittings corresponding to the foregoing description.

In the process of the invention, particularly in the vinylation of carboxylic acids, the mass ratio of catalyst phase to gas phase at the inlet of the reactor can be in the range from 1000/1 to 2/1, preferably in the range from 200/1 to 50/1.

The reactants can be fed in either after preheating, i.e. in the region of the reaction temperature, or cold. Owing to the high phase ratio to the catalyst phase, preheating can also occur by means of the process heat.

The heat of reaction can be removed by means of various heat exchangers. These heat exchangers do not have to be in the vicinity of the reaction space, but can also, if desired, be located outside the reactor. The individual heat flows are dependent on the specific heat of reaction and on the desired temperatures in the reactor and in the work-up apparatuses.

The heat of reaction which has been removed can thus be utilized very simply, e.g. in the process itself, for heating a distillation apparatus or for generating steam.

Figure 1:
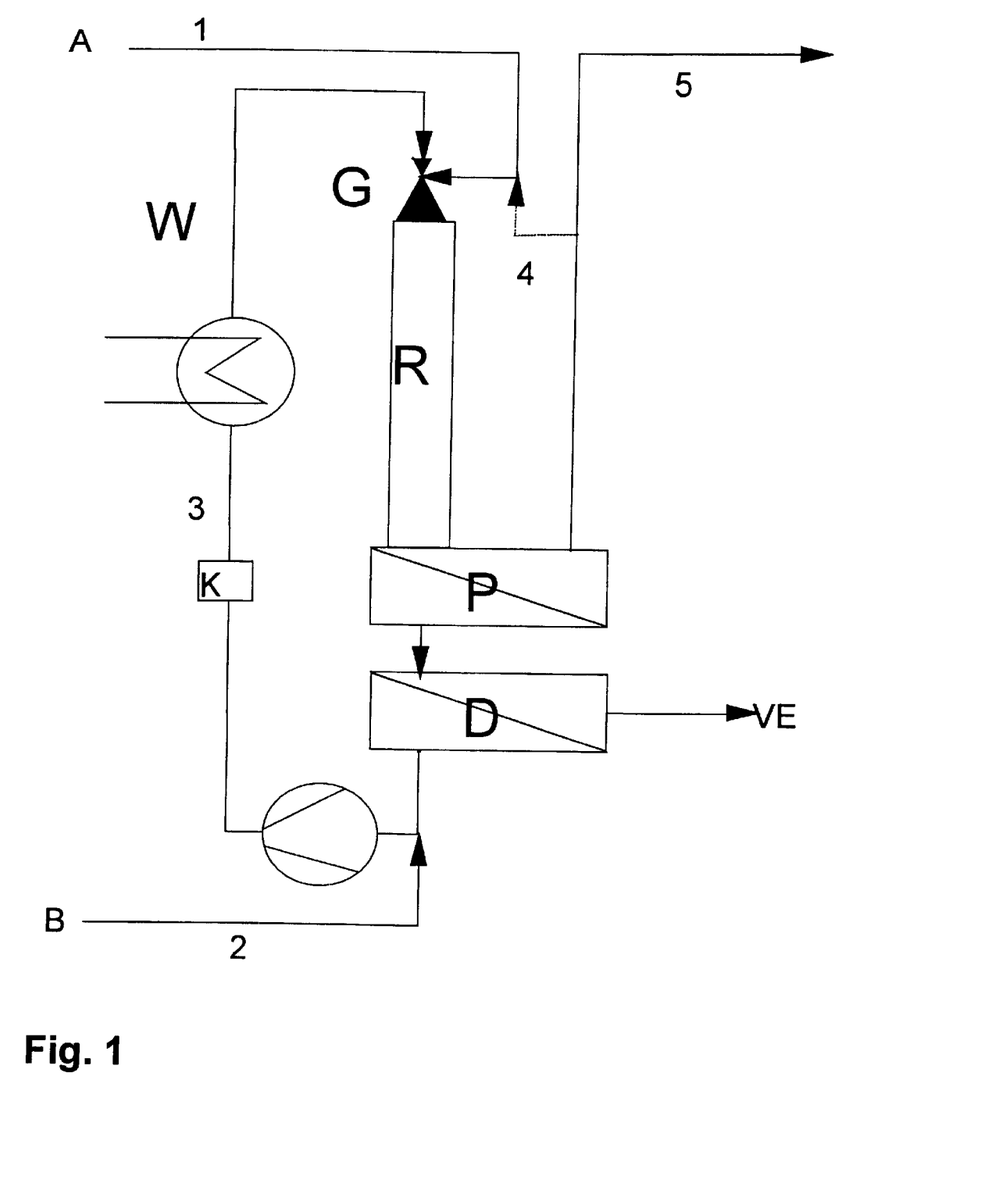
FIG. 1 is an apparatus embodiment of the process of the invention.

FIG. 1 shows a possible embodiment of the process of the invention, in which it is assumed that a gaseous starting material A reacts with a liquid starting material B in the presence of a liquid catalyst phase K. The catalyst phase K in the catalyst circuit stream 3 is pumped directly to the top of the reactor R; it is possible, if desired, for a liquid-jet gas compressor G. i.e. A jet nozzle, to be installed upstream of the reactor. The feed gas in stream 1 is fed in via the suction side of the liquid-jet gas compressor (or the Jet nozzle) G. If this is not present, the two streams are simply combined without further measures. After the reaction in the reactor R is complete, excess gas is separated off by customary engineering means (stream 5), e.g. by means of a degasser or a residence time vessel P. The organic phase goes to the vessel D for the actual product separation. The crude product VE can be separated from the catalyst phase by, for example, distillation or flash evaporation of the output from the reactor if the catalyst and any solvent used have boiling points higher than that of the product. Other engineering methods appropriate to the particular problem, for example extraction, pervaporation, etc., are also possible; the critical point is that the catalyst can be recovered and recirculated (stream 3). Apart from the circulation pump H, the heat exchanger W indicates the possibility of heating the reaction mixture in the case of endothermic reactions or cooling it in the case of exothermic reactions or of utilizing the heat of reaction in another way, e.g. for steam generation.

In general, purification of the product will be necessary downstream of the vessel D, and this can be carried out as customary by distillation, extraction or any other product purification method (not shown).

Furthermore, the tailgas can be circulated by means of the connection 4 between stream 5 and stream 1.

The reactor can also be operated in the upflow mode or in any other position. In the case of operation in the upflow mode, gas and catalyst are advantageously fed in at the bottom of the reactor and the degassing unit is located at the top of the reactor. After separation of product and catalyst phases, the catalyst is recirculated to the bottom of the reactor.

The process of the present invention is particularly suitable for the vinylation of carboxylic acids by means of acetylene. This is outlined in FIG. 2. The liquid-jet compressor (et nozzle) of FIG. 1 can be included if desired. The reactor is advantageously operated in the downflow mode and designed for a dimensionless loading factor B of greater than 0.8 at the inlet of the reactor. In the loading region B=0.8–1, the pressure drop is about equal to the static pressure, so that no pressure drop is apparent on the gas side. The acetylene can thus be fed in at atmospheric pressure or with a slight gauge pressure of not more than 300 mbar. Starting material A (stream 1) is in this case acetylene, starting material B (stream 2) is the carboxylic acid to be vinylated. The catalyst circuit (stream 3) consists of a solution of the zinc salt of the acid to be vinylated in excess carboxylic acid B.

In the process of the invention, the catalyst used can be a metal salt, preferably the zinc salt of the carboxylic acid to be vinylated.

Figure 2:
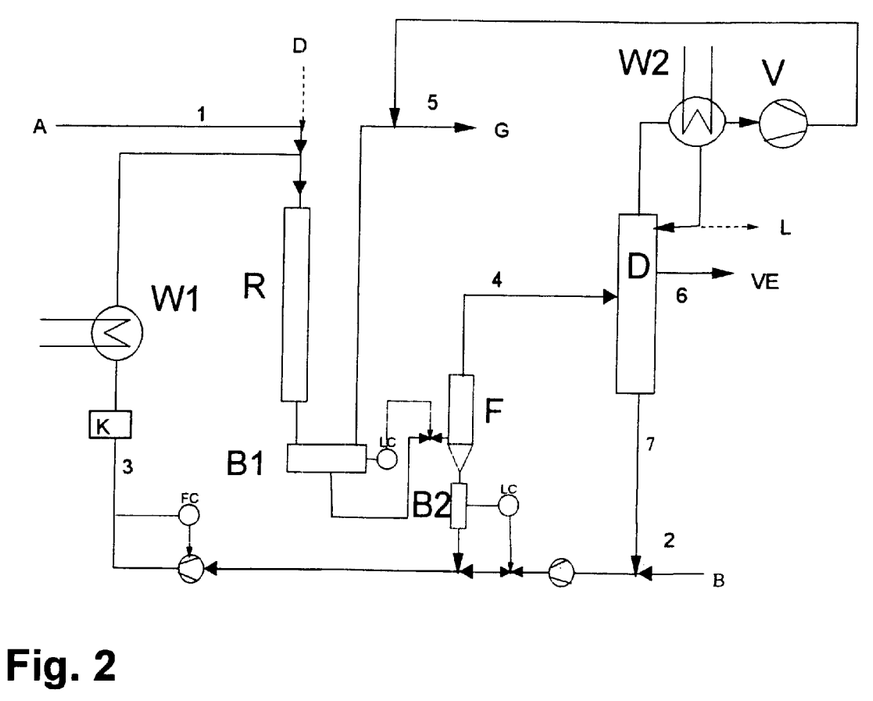
FIG. 2 is an apparatus embodiment of the process of the invention in which a carboxylic acid is vinylated with acetylene.

The catalyst is dissolved in excess carboxylic acid, so that in the present case the continuous phase is formed by the catalyst solution and the disperse phase is formed by acetylene.

As degasser, which is located downstream of the actual reactor R, use is made of a residence time vessel B1 which can be designed simultaneously as a buffer volume and working vessel.

Since vinyl esters have lower boiling points than the carboxylic acid used, they can be separated from the catalyst by thermal means, for example by distillation. A particularly favorable method, because it is gentle on the product, has been found to be preliminary separation of the catalyst from products in a flash vessel F, with the vapors, i.e. gaseous product, formed in the flash vessel being passed directly to a distillation column D in which the vinyl ester VE (stream 6) is separated from residual carboxylic acid (stream 7), which is also carried over from the single-stage separation in the flash vessel as a result of the partial vapor pressure.

The carboxylic acid obtained at the bottom of the column as stream 7 can be recirculated to the reaction together with fresh carboxylic acid to make-up the amount consumed. Flash vessel F and column D are operated under reduced pressure in the case of vinyl esters having a relatively high molecular weight and thus a relatively high boiling point, in which case the vacuum is advantageously set so that the boiling temperature is just below the desired reaction temperature. In this way, the heat of reaction can be utilized directly for the distillation.

Low boilers L are obtained at the top of the column D, and this material can generally be separated by occasional stripping of the runback. The vinyl ester withdrawn in the side stream 6 is highly pure and can be used directly for, for example, homopolymerization or copolymerization reactions. For prolonged storage, the vinyl ester should be admixed with a stabilizer in order to avoid undesirable autopolymerization.

A steam feed D can be additionally provided at the top of the reactor R. Here, small amounts of steam can be metered in so that the catalyst always contains a small amount of water, e.g. 0.1–0.5% by weight. Although this water inhibits the reaction slightly, it prevents the formation of anhydrides of the carboxylic acid which would no longer be available to the reaction and would have to be discharged as inert.

The catalyst circuit 3 is preferably operated at a constant flow (FC in FIG. 2), which results in very steady and stable behavior of the reactor. The crude product obtained in the degasser B1 is transferred under level control to the flash vessel F, and the liquid catalyst/carboxylic acid mixture separated goes to a reservoir B2 for the catalyst circuit pump.

The volume is constant throughout the entire plant, except for the reservoir B2. The decrease in level in B2 is a direct measure of the proportion of product removed in vapor form to the distillation column D, so that the level measurement in the vessel B2 is directly the control parameter for the amount of replacement carboxylic acid.

Having now generally described this invention, a further understanding can be obtained by reference to certain specific examples which are provided herein for purposes of illustration only and are not intended to be limiting unless otherwise specified.

EXAMPLES

Example 1 (Comparative Example)

The vinylation was conducted in an experimental apparatus (see FIG. 3), similar to that described in the literature (G. Hübner, Fette, Seifen Anstrichm. 68, 290 (1966), DE 1210810, DE 1238010). The reactor R had a height of 20 cm and a diameter of 10 cm and was packed with Raschig rings to improve mass transfer. The reactor was thermostated by means of a double wall. Acetylene A and the carboxylic acid C to be reacted were fed into the reactor through a frit at the bottom of the reactor R.

Figure 3:
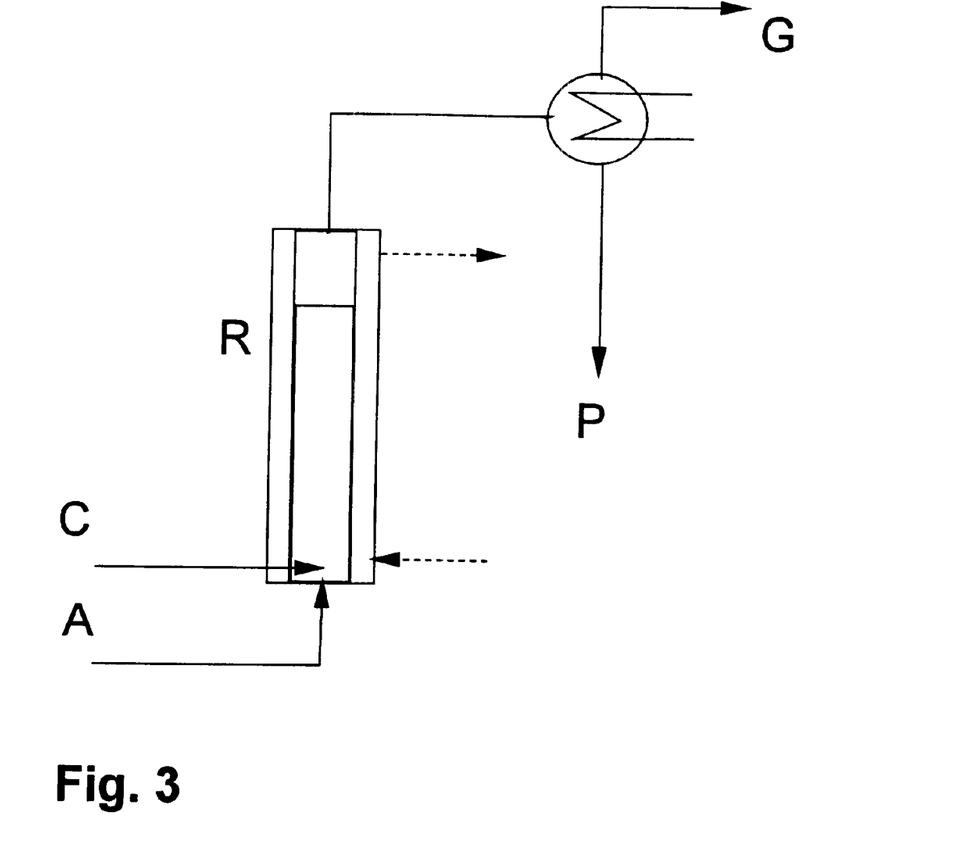
FIG. 3 is an apparatus embodiment of a comparative vinylation process.

The catalyst was the zinc salt of the acid to be vinylated, dissolved in an excess of acid. The reaction was conducted at a concentration ranging from 55–80% by weight of zinc salt in excess acid. The reactor charge was 1.35 liters.

In a modification of the procedure described in DE 1238010, the acetylene used was saturated with water at 40° C. rather than at 20° C., otherwise the catalyst resinifies too quickly. The product P was conducted with the waste gas together with unreacted carboxylic acid and condensed in the heat exchanger W. The waste gas G was discharged into a waste gas line.

The carboxylic acid used was a mixture of tertiary nonanoic acids having a purity of 99.73%, based on the content of tertiary nonanoic acids, and the following composition, wherein the amounts of acids are given in percent by weight:

| | |
|---|---|
| 2,2-Dimethylheptanoic acid | 7.31 |
| 2-Methyl-2-ethylhexanoic acid | 54.30 |
| 2-Methyl-2-propylpentanoic acid | 7.09 |
| 2,2-Diethylpentanoic acid | 3.40 |
| 2,2,5-Trimethylhexanoic acid | 0.83 |
| 2,2,4-Trimethylhexanoic acid | 0.81 |
| 2,4-Dimethyl-2-ethylpentanoic acid | 1.76 |
| 2,2,3-Trimethylhexanoic acid | 2.54 |
| 2-Methyl-2-isopropylpentanoic acid | 5.44 |
| 2,3-Dimethyl-2-ethylpentanoic acid A | 7.27 |
| 2,3-Dimethyl-2-ethylpentanoic acid B | 7.59 |
| 2-Ethyl-2-isopropylbutanoic acid | 1.19 |
| Other $C_9$ acids | 0.20 |
| impurities not determined | 0.27 |

In a series of experiments, the temperature dependence of the space-time yield (STY) was determined.

At a reaction temperature of 190° C., hardly any conversion took place. Only in the region above 230° C. were industrially interesting STYs of 0.3 t/m³/h achieved. In all experiments, the acetylene conversion was low, despite the fact that the carboxylic acid was present in a high excess. Circulating gas flows of acetylene of the order ranging from 100 mol. per mol. of vinyl ester formed at 190° C. to (in the best case) ~6 mol. per mol. at 235° C. have to be reckoned with.

From analyses of the waste gas, it was estimated that about 10% of the acetylene reacted had reacted to form acetaldehyde at 235° C. In addition, benzene, butenyne, crotonaldehyde and further low boilers not determined were found in the waste gas. The required prepressure of the acetylene was ~0.09 bar/m, so that a reactor with the permissible prepressure of 0.3 bar could not be more than 3 m high, since a certain pressure margin has to be allowed industrially for the pressure drop in lines and regulators.

| Experiment No. | 1 | 2 | 3 | 4 | 5 | 6 | 7 | 8 | 9 |
|---|---|---|---|---|---|---|---|---|---|
| Temperature [° C.] | 190 | 210 | 220 | 225 | 231 | 235 | 235 | 235 | 235 |
| Acetylene [mol/h] | 22.00 | 22.00 | 22.00 | 22.00 | 22.00 | 22.00 | 16.50 | 19.25 | 24.75 |
| Vinyl ester [mol/h] | 0.22 | 1.10 | 1.69 | 2.27 | 2.71 | 3.30 | 3.01 | 3.28 | 3.45 |
| Yield of vinyl ester based on acetylene used | 1.0% | 5.0% | 7.7% | 10.3% | 12.3% | 15.0% | 18.2% | 17.0% | 13.9% |
| STY [t/m³/h] | 0.03 | 0.15 | 0.23 | 0.31 | 0.37 | 0.45 | 0.41 | 0.45 | 0.47 |

Example 2 (Comparative Example)

Figure 4:
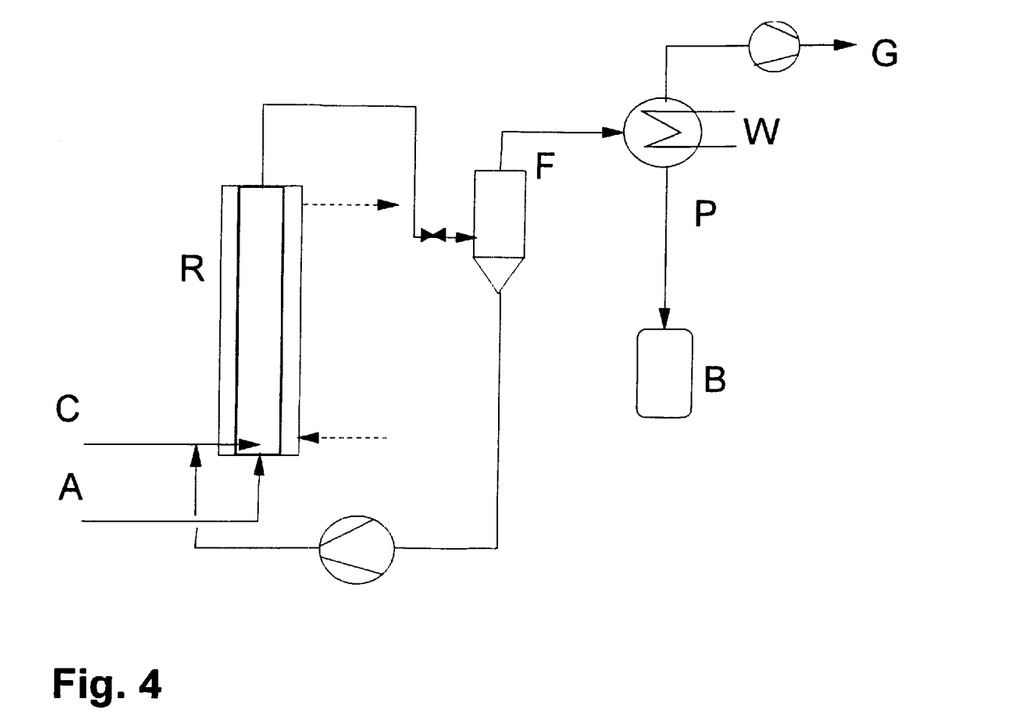
FIG. 4 is an apparatus embodiment containing Sulzer mixers of a comparative vinylation process.

This experiment was conducted using, as shown in FIG. 4, a double-wall, thermostatable reactor R which was provided with Sulzer mixers to improve mass transfer. The catalyst and fresh carboxylic acid C having the composition given in Example 1 were fed in at the bottom of the reactor R at a constant flow rate of 8 l/h. Acetylene A was fed in through a frit at a constant 4.5 mol/h. The output from the reactor was, after depressurization, passed through a thin film evaporator F operated at 80 mbar to remove the vinyl ester by distillation together with about 15% of carboxylic acid. This fact is taken into account in the vinyl ester balance.

In the heat exchanger W, the tailgas G was disposed of and the product phase P was collected in the vessel B.

The reactor was operated under the typical conditions for a bubble column and, therefore, not under the conditions of the process of the invention (B=0.27–0.52).

In addition, the influence of the water content of the catalyst phase was examined under otherwise constant conditions. This was achieved by feeding a small amount of steam into the acetylene feed and the water was determined in samples of the catalyst solution by Karl-Fischer titration.

Analyses of the zinc content and also density and viscosity determinations were conducted as a function of temperature on these samples. The corresponding data for acetylene were interpolated from tables.

Apparatus Parameters

| | | |
|---|---|---|
| Reactor DN40 | Length of the packed zone L | 1 m |
| | Diameter D | 0.0431 m |
| Packing | SMV8 DN 40 | (Sulzer) |
| | Hydraulic diameter $d_H$ | 0.0072 m |
| | Empty tube fraction | $\psi = 83\%$ |
| Catalyst | Circulation | 0.008 m³/h |
| | Zinc salt/carboxylic acid | 55–60% by weight of Zn salt |

Results

| Experiment No. | 10 | 11 | 12 | 13 |
|---|---|---|---|---|
| Temperature [° C.] | 190 | 190 | 190 | 190 |
| Water content [wt %] | 0.12% | 0.21% | 0.38% | 0.72% |
| Cat. circulation [m$^3$/h] | 0.008 | 0.008 | 0.008 | 0.008 |
| Cat. circulation [kg/h] | 7.336 | 7.336 | 7.336 | 7.336 |
| ρ of cat. [kg/m$^3$] | 917 | 917 | 917 | 917 |
| η of cat. [Pa*s] | 1.92E-02 | 1.53E-02 | 9.27E-03 | 2.07E-03 |
| ρ of acetylene [kg/m$^3$] | 0.68 | 0.68 | 0.68 | 0.68 |
| η of acetylene [Pa*s] | 1.53E-05 | 1.53E-05 | 1.53E-05 | 1.53E-05 |
| Acetylene in [mol/h] | 4.50 | 4.50 | 4.50 | 4.50 |
| Acetylene out [mol/h] | 2.16 | 2.72 | 2.97 | 3.36 |
| Acetylene in [kg/h] | 0.117 | 0.117 | 0.117 | 0.117 |
| Acetylene out [kg/h] | 0.056 | 0.071 | 0.077 | 0.087 |
| Acetylene in [m$^3$/h] | 0.171 | 0.171 | 0.171 | 0.171 |
| Acetylene out [m$^3$/h] | 0.048 | 0.061 | 0.067 | 0.075 |
| Acetylene conversion | 52.1% | 39.6% | 34.0% | 25.3% |
| PD [bar] | 2.14E-03 | 1.98E-03 | 1.68E-03 | 1.10E-03 |
| PS [bar] | 4.09E-03 | 4.09E-03 | 4.09E-03 | 4.09E-03 |
| B | 0.52 | 0.49 | 0.41 | 0.27 |
| Vinyl ester [kg/h] | 0.42 | 0.31 | 0.28 | 0.18 |
| STY [t/m$^3$/h] | 0.27 | 0.20 | 0.18 | 0.12 |

The conversions of acetylene are still low, although the disadvantage of the product having to be discharged with the waste gas as in Example 1 is eliminated by the flash separation. However, in industrial implementation, this still requires an acetylene gas circulation of the order of 2–4 mol/mol, based on vinyl ester formed. In addition, the required prepressure is in a similar range to that in Example 1, so that a maximum reactor height of about 3 m is possible from an engineering point of view.

Example 3 (Process According to the Invention)

The process of the invention was tested in a pilot plant as shown in FIG. 2 using the same tertiary nonanoic acid as described in Examples 1 and 2.

The reactor R was a DN 40 tube packed with a knitted wire mesh from VFF (Vereinigte Fülikörper Fabriken, Type T-20-M) as is used for the production of droplet precipitators, also known as demister packing (Experiments 14, 15, 16). The knitted wire mesh was rolled more tightly than usual and was packed into the reactor so that a greater packing density and thus a smaller hydraulic diameter and a smaller empty tube fraction resulted. The length of the packing was 2000 mm. The empty tube fraction was determined by measuring the volume of the empty and packed reactor, while the packing density was determined by weighing the installed packing. The resulting packing parameters are indicated in the individual experiments. A liquid-jet compressor was installed upstream of the reactor in experiments 14, 15 and 16. An annular diaphragm could be installed at the bottom of the reactor to make it possible to increase the pressure at the reactor outlet. The pressure drop over the length of the packing was determined by means of a differential pressure measurement.

For experiment 17, the knitted wire mesh was removed and replaced by Sulzer mixers (Type SMV 8 ON 40). In addition, the liquid-jet gas compressor was omitted.

The catalyst stream comprising 65% by weight of the zinc salt of the carboxylic acid to be vinylated dissolved in excess acid was fed in at the top of the reactor. The acetylene was metered in via the suction side of the liquid-jet compressor (experiments 14, 15, 16). In experiment 17, the acetylene was introduced directly into the catalyst circuit via a tube directly upstream of the top of the reactor without further mixing aids. In this experiment, no regulation whatever of the acetylene feed was employed. Only the consumption which is automatically established at the existing acetylene admission pressure from the line (about 200 mbar) was measured.

In all experiments, small amounts of steam were fed into the acetylene so that the catalyst had, according to analyses, a water content of 0.25±0.05% by weight.

The output from the reactor was degassed in the residence time vessel B1 and fed under level control to the evaporator F (flash evaporation under reduced pressure). The vapors were passed to a distillation column D and were fractionated into low boilers L, which were stripped from the column runback from time to time, high boilers (together with carboxylic acid in accordance with the partial vapor pressure) which were obtained at the bottom and the vinyl ester of the carboxylic acid used, which was withdrawn as the side stream 6. Column and flash vessel were maintained at a reduced pressure of 80–100 mbar by means of a vacuum compressor.

The liquid output from the evaporator was conveyed via the intermediate vessel B2 and a circulation pump LC back to the reactor. The feed of carboxylic acid, consisting of the bottoms from the distillation column supplemented by fresh carboxylic acid, was controlled via the level in B2.

The formation of by-products was so low that it could no longer be balanced. From long-term tests over a period of one week in each case, it was estimated that the total by-product formation was less than 1% of the total conversion.

No decrease in the catalyst performance was observed either. Just the regular removal of analytical samples was obviously sufficient to bleed off high boilers and other interfering substances which may have been formed.

| Experiment | Sequential No. | — | 14 | 15 | 16 | 17 |
|---|---|---|---|---|---|---|
| Reactor | Length | m | 2 | 2 | 2 | 2 |
| | Diameter | m | 4.30E-02 | 4.30E-02 | 4.30E-02 | 4.30E-02 |
| Packing | Type | — | T-20-M | T-20-M | T-20-M | SMV8DN |
| | Hydraulic diam. | m | 4.71E-03 | 4.71E-03 | 4.71E-03 | 7.20E-03 |
| | Empty tube fraction | % | 96.7% | 96.7% | 96.7% | 83.0% |
| Operating data | Temperature | ° C. | 190 | 190 | 190 | 191 |
| | Prepressure | bar | 1.46 | 1.9 | 1.73 | 1.04 |
| | Back pressure | bar | 1.04 | 1.7 | 1.35 | 1.04 |

-continued

| Experiment | Sequential No. | — | 14 | 15 | 16 | 17 |
|---|---|---|---|---|---|---|
| Catalyst | Circuit 1) | m³/h | 1.1 | 1.1 | 1.1 | 1.3 |
|  | Zinc salt | wt-% | 65 ± 5% | 65 ± 5% | 65 ± 5% | 65 ± 5% |
| Acetylene | Feed | mol/h | 17.43 | 21.62 | 21.62 | 10.86 |
| Vinyl ester | Production | mol/h | 16.50 | 20.82 | 20.11 | 9.33 |
| Acetylene | Excess | mol/mol | 1.056 | 1.038 | 1.075 | 1.163 |
| Vinyl ester | STY | t/m³/h | 1.047 | 1.321 | 1.276 | 0.592 |
| PS in | M/v*g in | mbar/m | 63 | 64 | 62 | 69 |
| PS out | M/v*g out | mbar/m | 85 | 89 | 87 | 87 |
| PD in | $P_{lg}$/L in | mbar/m | 472 | 492 | 492 | 86 |
| PD out | $P_{lg}$/L out | mbar/m | 143 | 141 | 141 | 67 |
| Factor B | reactor in | — | 7.45 | 7.66 | 7.87 | 1.24 |

In experiment 14, an extraordinarily high space-time yield of over 1 t/m³/h was achieved at a very low temperature typical of the process of only 190° C. A further improvement in the space-time yield could be achieved by slightly increasing the pressure (experiments 15, 16).

The acetylene excess was minimal, so that circulation of acetylene could be omitted. In particular, the waste gas was no longer measurable in experiment 15.

Finally, in experiment 17, the catalyst circulation was set so that the gas-side differential pressure above the reactor was zero, i.e. pressure drop and static pressure were eliminated. Nevertheless, the reactor was flooded and operated quietly and without trouble. The acetylene uptake established by itself led to a still very high space-time yield of almost 0.6 t/m³/h, so that a reactor of any length (possibly with multiple injection of acetylene) could be operated without problems at the permissible acetylene prepressure of not more than 300 mbar.

Example 4 (Process According to the Invention)

Preliminary experiments on the vinylation of 2-ethylhexanoic acid (2EHA) were conducted in the experimental plant described in Example 3. Without further optimization, industrially interesting space-time yields of 0.3 t/m³/h were achieved here too, although this acid is much more difficult to vinylate than is a tertiary carboxylic acid.

| Experiment | Seq. No. | — | 18 | 19 | 20 |
|---|---|---|---|---|---|
| Carboxylic acid |  | — | 2EHA | 2EHA | 2EHA |
| Reactor | Length | m | 2 | 2 | 2 |
|  | Diameter | m | 4.30E-02 | 4.30E-02 | 4.30E-02 |
| Packing | Type | — | SMV8DN40 | SMV8DN40 | SMV8DN40 |
|  | Hydr. diam. | m | 7.20E-03 | 7.20E-03 | 7.20E-03 |
|  | Empty tube fraction | % | 83.0% | 83.0% | 83.0% |
| Operating data | Temperature | °C | 200 | 195 | 190 |
|  | Pre-pressure | bar | 1.114 | 1.114 | 1.114 |
|  | Back pressure | bar | 1.04 | 1.04 | 1.04 |

-continued

| Experiment | Seq. No. | — | 18 | 19 | 20 |
|---|---|---|---|---|---|
| Catalyst | Circulation | m³/h | 1.33 | 1.33 | 1.32 |
|  | Zinc salt | wt-% | 65 ± 5% | 65 ± 5% | 65 ± 5% |
| Acetylene | Feed | mol/h | 8.739 | 6.757 | 7.432 |
| Vinyl ester | Production | mol/h | 5.65 | 3.70 | 4.90 |
| Acetylene | Excess | mol/mol | 1.548 | 1.825 | 1.518 |
| Vinyl ester | STY | t/m³/h | 0.331 | 0.217 | 0.287 |
| PS in | M/V · g in | mbar/m | 73 | 76 | 75 |
| PS out | M/V · g out | mbar/m | 83 | 86 | 85 |
| PD in | $P_{lg}$/L in | mbar/m | 129 | 134 | 140 |
| PD out | $P_{lg}$/L out | mbar/m | 106 | 110 | 116 |
| Factor B | Reactor in | — | 1.78 | 1.76 | 1.86 |

Example 5 (Process According to the Invention)

Carboxylic acids having relatively short aliphatic chains, e.g. butyric acid, are generally not able to be vinylated by the zinc salt method, since the required reaction temperatures of usually >200° C. cannot be achieved because of the high vapor pressure of the acids. For example, butyric acid has a boiling point of 165.5° C. at atmospheric pressure of 1013 mbar.

The experiments were carried out as described in Examples 3 and 4, with a liquid-jet gas compressor (jet nozzle) for feeding in the acetylene being installed upstream at the reactor. The reaction temperature was selected so as to be below the boiling point of the zinc salt/butyric acid mixture.

In experiment 21, use was made of a reactor packed with 6*6 mm wire mesh rings. These wire mesh rings are customarily employed in distillation technology (VFF= Vereinigte Fülikörper Fabriken).

| Experiment | Sequential No. | — | 21 | 22 | 23 | 24 |
|---|---|---|---|---|---|---|
| Reactor | Length | m | 2 | 2 | 2 | 2 |
|  | Diameter | m | 6.40E-02 | 4.30E-02 | 4.30E-02 | 4.30E-02 |
| Packing | Type | — | MDR 6*6 | SMV8DN40 | SMV8DN40 | SMV8DN40 |
|  | Hydraulic diam. | m | 2.55E-03 | 7.20E-03 | 7.20E-03 | 7.20E-03 |
|  | Empty tube fraction | % | 91.5% | 83.0% | 83.0% | 83.0% |
| Operating data | Temperature | °C. | 180 | 167 | 177 | 177 |
|  | Prepressure | bar | 1.06 | 2 | 2 | 2.35 |
|  | Back pressure | bar | 1.04 | 2.00 | 2 | 2.3 |
| Catalyst | Circulation 1) | m³/h | 1.04 | 1.59 | 1.26 | 1.26 |
|  | Zinc salt | wt-% | 50.0% | 55.0% | 84.2% | 84.2% |
| Acetylene | Feed | mol/h | 5.14 | 6.31 | 10.405 | 11.937 |
| Vinyl ester | Production | mol/h | 1.52 | 1.91 | 4.20 | 5.34 |
| Acetylene | Excess | mol/mol | 3.37 | 3.30 | 2.48 | 2.23 |
| Vinyl ester | STY | t/m³/h | 0.027 | 0.075 | 0.17 | 0.21 |
| PS in | $M/v \cdot g$ in | mbar/m | 88 | 97 | 90 | 90 |
| PS out | $M/v \cdot g$ out | mbar/m | 99 | 103 | 99 | 100 |
| PD in | $P_{1g}/L$ in | mbar/m | 239 | 146 | 99 | 99 |
| PD out | $P_{1g}/L$ out | mbar/m | 113 | 119 | 78 | 78 |
| Factor B | reactor in | — | 2.72 | 1.50 | 1.10 | 1.10 |

In experiment 21 (atmospheric pressure), slight formation of vinyl ester is observed. However, a significant increase in the space-time yield is once again achieved by increasing the pressure, increasing the zinc salt content of the catalyst and a moderate ethylene excess (circulating gas operation). Experiment 24 achieves an STY of 0.21 t/m³/h which already represents an industrially sensible order of magnitude. Thus, even lower carboxylic acids such as butyric acid can be vinylated by the process of the invention.

The disclosure of German priority Application Number 19 925 385.4 filed Jun. 2, 1999 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein

What is claimed as new and is intended to be secured by Letters Patent is:

1. A process for conducting catalytic multiphase reactions, comprising:

conducting the catalytic multiphase reactions in a tube reactor, wherein the catalyst is present in the continuous phase and at least one starting material is present in a dispersed phase and the loading factor B of the tube reactor is equal to or greater than 0.8.

2. The process as claimed in claim 1, wherein carboxylic acids are reacted with acetylene in the multiphase reaction to give the corresponding vinyl esters.

3. The process as claimed in claim 2, wherein carboxylic acids are reacted with acetylene in the multiphase reaction such that the weight ratio of the catalyst phase to gas phase at the inlet of the reactor ranges from 1000/1 to 2/1.

4. The process as claimed in claim 3, said weight ratio ranges from 200/1 to 50/1.

5. The process as claimed in claim 2, wherein the carboxylic acid contains from 2 to 16 carbon atoms.

6. The process as claimed in claim 5, wherein the carboxylic acid is selected from the group consisting of pivalic acid, 2-ethylhexanoic acid, neononanoic acid, decanoic acid, undecanoic acid, lauric acid and tridecanoic acid.

7. The process as claimed in claim 2, wherein the catalyst is a metal salt of the carboxylic acid being reacted.

8. The process as claimed in claim 7, wherein the catalyst is the zinc salt of the carboxylic acid.

9. The process as claimed in claim 1, wherein the loading factor B is greater than or equal to 0.9.

10. The process as claimed in claim 1, wherein the loading factor B is greater than or equal to 1.0.

11. The process as claimed in claim 1, wherein said continuous phase and the disperse phase or phases are present in a weight ratio of continuous phase to disperse phase(s) greater than 2.

12. The process as claimed in claim 1, wherein the continuous phase drives a jet nozzle upstream of the tube reactor.

13. The process as claimed in claim 1, wherein at least one starting material is dispersed by means of the energy introduced into the tube reactor by the continuous phase.

14. A method of synthesizing homopolymers or copolymers, comprising:

conducting homopolymerization or copolymerization with a vinyl ester, wherein said vinyl ester is prepared by conducting a catalytic multiphase reaction of a carboxylic acid with acetylene in a tube reactor, wherein the catalyst is present in the continuous phase and at least one of the carboxylic acid and the acetylene is present in a dispersed phase and the loading factor B of the tube reactor is equal to or greater than 0.8.

15. A method of preparing an adhesive, comprising:

preparing said adhesive utilizing a vinyl ester, wherein said vinyl ester is prepared by conducting a catalytic multiphase reaction of a carboxylic acid with acetylene in a tube reactor, wherein the catalyst is present in the continuous phase and at least one of the carboxylic acid and the acetylene is present in a dispersed phase and the loading factor B of the tube reactor is equal to or greater than 0.8.

* * * * *